United States Patent [19]

Adams, Jr. et al.

[11] 4,053,299
[45] Oct. 11, 1977

[54] NOVEL THIOTRIAZINEDIONES AND THEIR USE AS HERBICIDES

[75] Inventors: John Benjamin Adams, Jr., Hockessin; Richard Lee Ellis, Wilmington; Kang Lin, Newark, all of Del.

[73] Assignee: E. I. Du Pont de Nemours and Company, Wilmington, Del.

[21] Appl. No.: 621,401

[22] Filed: Oct. 10, 1975

[51] Int. Cl.$^2$ .............. C07D 251/46; A01N 9/22; A01N 9/12
[52] U.S. Cl. .............................. 71/93; 544/211; 544/194
[58] Field of Search .............. 260/248 NS, 249.5; 424/249; 71/93

[56] References Cited
U.S. PATENT DOCUMENTS

| | | | |
|---|---|---|---|
| 3,850,924 | 11/1974 | Fuchs et al. | 260/249.5 |
| 3,902,887 | 9/1975 | Lin | 260/249.5 |
| 3,933,815 | 1/1976 | Ploeg | 260/249.5 |
| 3,951,971 | 4/1976 | Fuchs et al. | 260/249.5 |

Primary Examiner—John M. Ford

[57] ABSTRACT

Thiotriazinediones of the formula:

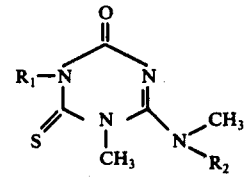

where
$R_1$ is certain organic radicals; and
$R_2$ is alkyl of 1-4 carbons are useful as herbicides. The most preferred compound is 3-cyclohexyl-6-dimethylamino-1-methyl-2-thio-s-triazine-2,4(1H,3H)-dione.

12 Claims, No Drawings

NOVEL THIOTRIAZINEDIONES AND THEIR USE AS HERBICIDES

BACKGROUND OF THE INVENTION

U.S. Pat. No. 3,873,540 to Fuchs and Lin discloses a class of s-triazines of the general formula:

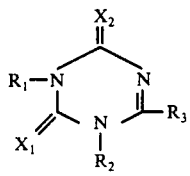

where $X_1$ and $X_2$ are each independently oxygen or sulphur;
$R_1$ is certain organic radicals including certain cyclic radicals;
$R_2$ is certain lower alkyl radicals; and
$R_3$ is $SR_4$ or $OR_4$ where $R_4$ is certain organic radicals, including certain lower alkyl radicals.

These compounds are disclosed as being useful as herbicides.

U.S. Pat. No. 3,902,887 to Lin discloses a class of s-triazines of the general formula:

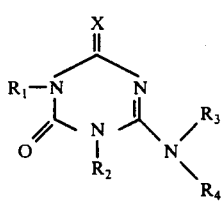

where

X is oxygen or sulfur;
$R_1$ is certain organic radicals including certain open and cyclic radicals;
$R_2$ is hydrogen, lower alkyl, or certain cations;
$R_3$ is hydrogen or certain lower alkyls; and
$R_4$ is certain organic radicals.

These compounds are disclosed as being useful as herbicides.

SUMMARY OF THE INVENTION

The invention comprises novel compounds of the formula I:

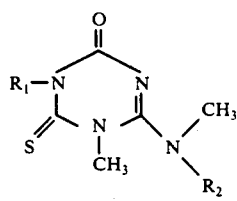

where $R_1$ is alkyl of 3-6 carbons; cycloalkyl of 5-8 carbons; cycloalkyl of 5-8 carbons substituted with 1 methyl group; cyclohexyl substituted with 1 trifluoromethyl group, or with 2-4 methyl groups; cyclohexenyl; decahydronaphth-1-yl; 3-trifluoromethylphenyl; or

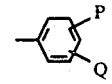

where

P is hydrogen, methyl, chlorine or fluorine; and
Q is hydrogen or chlorine; and
$R_2$ is alkyl of 1-4 carbons;
which are useful as herbicides.

Preferred for their herbicidal activity are those compounds of formula I where $R_2$ is methyl. Also preferred for their high activity are those compounds of formula I where $R_1$ is cyclopentyl optionally substituted with one methyl group or where $R_1$ is cyclohexyl optionally substituted with one trifluoromethyl group or one or two methyl groups.

Specifically preferred for its herbicidal activity is the compound 3-cyclohexyl-6-dimethylamino-1-methyl-2-thio-s-triazine-2,4(1H,3H)-dione.

The invention also includes the method for the control of undesirable vegetation comprising applying to the locus of such undesired vegetation an herbicidally effective amount of a compound of formula I and compositions for the control of undesirable vegetation comprising an herbicidally effective amount of a compound of formula I and at least one of (a) an inert diluent and (b) a surfactant.

DETAILED DESCRIPTION OF THE INVENTION

The 2-thio-s-triazine-2,4(1H,3H)-diones (formula I) of this invention can be prepared by either of two general routes: (a) thiocarbonyldiimidazole route, and (b) phosgene-thiourea route.

Equation 1 depicts the preparation of the compounds by the reaction of carbamoylguanidines (formula II) with 0.9 to 1.1 equivalents of thiocarbonyldiimidazole in refluxing organic solvents such as tetrahydrofuran, which do not contain active hydrogen atoms. The time required to bring about the ring closure depends on the reactivity of the guanidine being used and the reflux temperature of the solvent.

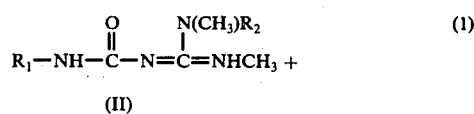

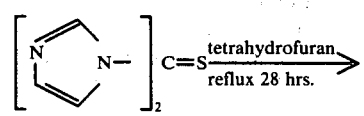

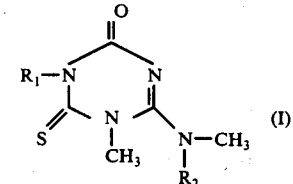

The carbamoylguanidine starting compounds of formula II are readily prepared by standard synthetic methods from dialkylcyanamides as shown below.

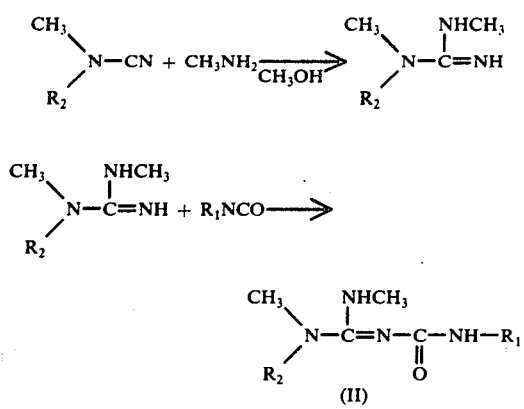

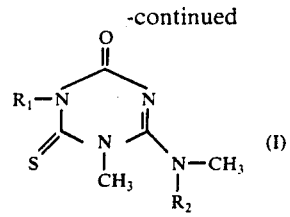

EXAMPLE I

3-Cyclohexyl-6-dimethylamino-1-methyl-2-thio-s-triazine-2,4(1H,3H)-dione

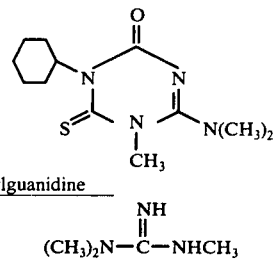

(a) 1,1,3-Trimethylguanidine $$(CH_3)_2N-\overset{NH}{\underset{\|}{C}}-NHCH_3$$

A mixture of 140 parts of dimethylcyanamide, 300 parts of methanol, and 120 parts of methylamine is placed in a pressure bomb and heated for 7.75 hours on a steam bath; after cooling, the bomb is opened. Analysis by gas chromatography indicates that all starting material has reacted. After evaporating the solvent and excess amine under reduced pressure, the residue is distilled, yielding 108.2 parts of 1,1,3-trimethylguanidine, b.p. 85°–95° C/5 mm Hg.

b. 2-Cyclohexylcarbamoyl-1,1,3-trimethylguanidine

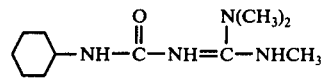

To 60.6 parts by weight of 1,1,2-trimethylguanidine in 600 parts by volume of toluene are added dropwise with cooling 75 parts by weight of cyclohexyl isocyanate. After evaporation of the solvent in vacuo, the product is recrystallized from acetonitrile to yield 2-cyclohexylcarbamoyl-1,1,3-trimethylguanidine, m.p. 121°–124° C.

c.

3-Cyclohexyl-6-dimethylamino-1-methyl-2-thio-s-triazine-2,4(1H,3H)-dione

To a solution of 49 parts by weight of 2-cyclohexylcarbamoyl-1,1,3-trimethylguanidine in 550 parts by weight of tetrahydrofuran is added 42 parts by weight of 90% thiocarbonyldiimidazole. The mixture is refluxed for 28 hours under nitrogen and then concentrated in vacuo. The residue is dissolved in chloroform and the solution washed with water, dried over magnesium sulfate, filtered and concentrated to a yellow-orange solid. Recrystallization from acetonitrile yields the product, 3-cyclohexyl-6-dimethylamino-1-methyl-2-thio-s-triazine-2,4(1H,3H)-dione.

EXAMPLE II

The following compounds can be prepared from the appropriate starting materials using the procedure described in parts (b) and (c) of Example I:

By using the methyl ester of 1-thio-4-alkylallophanimidic acid (formula III) in place of the guanidine reagent of equation 1, one obtains products wherein the 6-(methylalkylamino) group of the product of equation 1 is replaced by a methylthio group. This reaction is shown in equation 5 below.

The alkylallophanimidic acid of formula III for equation 5 is readily prepared by standard carbamylation of 1,2-dimethyl-2-thiopseudourea with an isocyanate:

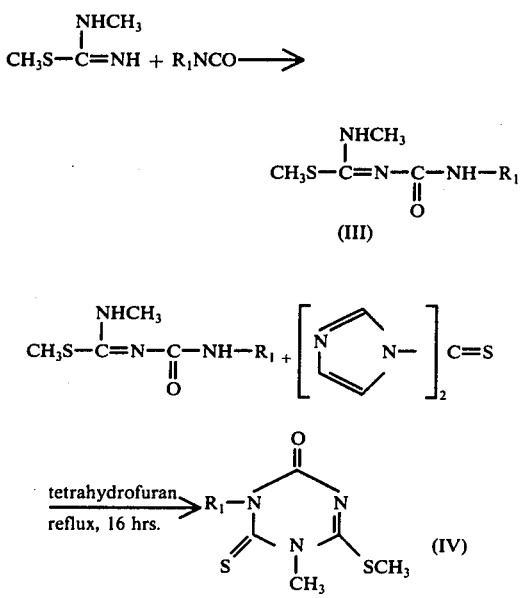

Reaction of the 6-methylthio triazine of formula IV shown in equation 5 with at least one equivalent dimethylamine or an alkylmethyl amine, R₂ (CH₃)NH, yields the corresponding 6-dimethylamino or 6-alkylmethylamino thiotriazinediones as shown in equation 6.

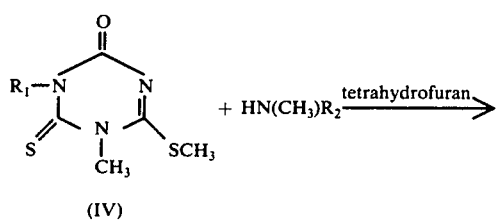

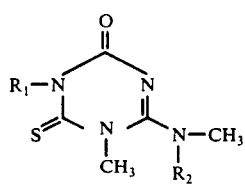

| Example | R₁ | R₂ |
|---------|-----|-----|
| IIa | (CH₃)₂CH— | CH₃ |
| b | CH₃(CH₂)₅— | CH₃ |
| c | cyclopropyl— | CH₃ |
| d | cycloheptyl— | CH₃ |
| e | 2-methylcyclopropyl— | CH₃ |
| f | 2-methylcycloheptyl— | CH₃ |
| g | 4-trifluoromethyl-thian-2-yl— | CH₃ |
| h | 3,4-dimethylcyclohexyl— | CH₃ |
| i | 2,3,4-trimethylcyclohexyl— | CH₃ |
| j | cyclohex-2-en-1-yl— | CH₃ |
| k | 1-methyl-thiochroman-yl (bicyclic dithia)— | CH₃ |
| l | 3-trifluoromethylphenyl— | CH₃CH₂— |
| m | 4-methylphenyl— | (CH₃)₂CH— |
| n | 4-chlorophenyl— | CH₃(CH₂)₃— |
| o | 3-fluorophenyl— | CH₃ |
| p | 3,4-dichlorophenyl— | CH₃ |
| q | 3-chloro-4-fluorophenyl (Cl, F substituted phenyl)— | CH₃ |

EXAMPLE III

3-Cyclohexyl-6-(N-methyl-N-ethanylamino)-1-methyl-2-thio-s-triazine-2,4(1H,3H)-dione

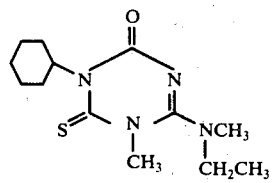

To a stirred mixture of 22.5 parts of N-methylthiourea in 100 parts of water is added, dropwise over 20 minutes, 32 parts of dimethyl sulfate, the temperature being maintained at 25° C by external cooling. When the reaction is no longer exothermic, the temperature is lowered to 0° C for 2 hours; the acid salt of N,S-dimethylpseudothiourea is formed but not isolated.

110 parts of toluene is added to the aqueous reaction mixture while maintaining the temperature at 0°–5° C, the pH of the stirred solution is adjusted to 9.5 ± 0.3 by the addition of 50% aqueous sodium hydroxide. To this solution is added, dropwise over 2 hours, 31.2 parts of cyyclohexyl isocyanate, while maintaining pH 9.5 ± 0.3 by simultaneous addition of 50% sodium hydroxide. The reaction mixture is transferred to a separatory funnel and the toluene layer removed. The toluene solution is dried with magnesium sulfate, and then diluted with approximately 1.5 volumes of heptane; the resultant white solid is filtered, washed with toluene-heptane (1:1) and heptane, and dried to yield 44 parts of methyl 4-cyclohexyl-N-methyl-1-thioallophanimidate, m.p. 121°–122.5° C.

To a solution of 4.6 parts by weight of methyl 4-cyclohexyl-N-methyl-1-thioallophanimidate in 20 parts by weight of dry tetrahydrofuran is added over a 1 hour period 3.95 parts by weight of thiocarbonyldiimidazole in 80 parts by weight of dry tetrahydrofuran. The reaction mixture is stirred 16 hours, and the solvent is removed by evaporation. The desired product is purified by chromatography on alumina (activity II), eluting with a 2:1 methylene chloride-ether solvent mixture. The product, 3-cyclohexyl-1-methyl-6-methylthio-2-thio-s-triazine-2,4(1H,3H)-dione, m.p. 133°–5° C comes off the column prior to the unreacted thioallophanimidate.

To a solution of 30.2 parts by weight of the 3-cyclohexyl-1-methyl-6-methylthio-2-thio-s-triazine-2,4(1H,3H)-dione in 600 parts by volume of tetrahydrofuran is added 4.5 parts of N-ethyl-N-methylamine with stirring. The mixture is allowed to stand for 1 day, after the addition, and then cooled and the desired product, 3-cyclohexyl-6-(N-methyl-N-ethylamino)-1-methyl-2-thio-s-triazine-2,4(1H,3H)-dione, isolated.

EXAMPLE IV

Using the appropriate amines and 6-methylthio-2-thiotriazinediones, in the procedure of Example III, the following compounds of formula I may be prepared.

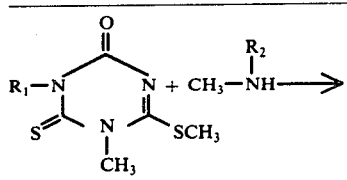

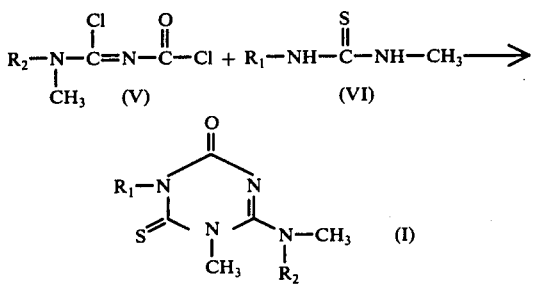

| Example | $R_1$ | $R_2$ |
|---------|-------|-------|
| IVa | $CH_3(CH_2)_4-$ | $CH_3-$ |
| b | $(CH_3)_3C-CH_2-$ | $CH_3-$ |
| c | $CH_3-\langle S \rangle-$ | $CH_3-$ |
| d | $CF_3-\langle S \rangle-$ | $CH_3CH_2-$ |
| e | $\begin{smallmatrix}CH_3\\CH_3\end{smallmatrix}\rangle\langle S \rangle-$ | $(CH_3)_2CH-$ |
| f | $\begin{smallmatrix}CH_3\\CH_3\\CH_3\end{smallmatrix}\rangle\langle S \rangle-$ | $CH_3-$ |
| g | $\langle\rangle^{CH_3}-$ | $CH_3-$ |
| h | $F-\langle\rangle-$ | $CH_3CH_2-$ |

A preferred method of preparing the compounds of this invention is by reaction of an N-alkyl-N-methyl-N'-chlorocarbonyl carbamidoyl chloride (formula V) with a 1-substituted-3-methylthiourea (formula VI) according to equation 7.

$$R_2-\underset{\underset{CH_3}{|}}{N}-\overset{\overset{Cl}{|}}{C}=N-\overset{\overset{O}{\|}}{C}-Cl + R_1-NH-\overset{\overset{S}{\|}}{C}-NH-CH_3 \longrightarrow$$
(V) (VI)

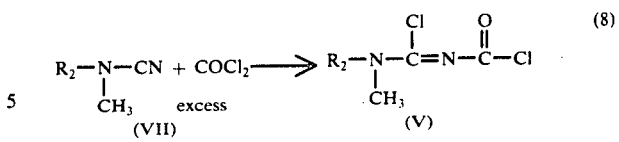

(7)

The thioureas utilized are commercially available and the N-alkyl-N-methyl-N'-chlorocarbonyl carbamidoyl chloride (formula V) can be prepared by reacting N-alkyl-N-methyl cyanamide (formula VII) with an excess of phosgene according to equation 8.

The reaction of the cyanamide and phosgene is carried out at a temperature between 0°–100° C with a preferred temperature of 10°–30° C for purity of product and 30°–70° C for economical operation. Suitable solvents for the reaction are aromatic solvents such as toluene or benzene and other inert organic solvents or the reaction can be carried out without solvent in excess phosgene. The ratio of phosgene to cyanamide can be from 1:1 to 10:1 with 2:1 to 3:1 being preferred. Pressure can be from atmospheric to 10 atmospheres.

The reaction of the carbamidoyl chlorides and thioureas is carried out at a temperature between 0°–100° C with a preferred temperature of 10°–30° C for purity of product and 30°–70° C for economical operation. Suitable solvents for the operation are halogen-substituted aliphatics, ethers, halogen- and alkyl-substituted aromatics or other inert organic solvent. The ratio of carbamidoyl chloride to thioureas is from 0.9 to 1.1.

EXAMPLE V

3-Cyclohexyl-1-methyl-6-dimethylamino-2-thio-s-triazine-2,4(1H,3H)-dione

In a flask equipped with an acetone-dry ice condenser, drying tube, mechanical stirrer and addition funnel, a mixture of 59.0 grams (0.60 mole) phosgene, 250 ml. anhydrous toluene and 20.0 grams anhydrous sodium carbonate powder is prepared. The purpose of the sodium carbonate is to remove traces of hydrogen chloride. The mixture is stirred for 0.5 hour and then treated dropwise with stirring over a 20 minute period at room temperature with a solution of 20.0 grams (0.29 mole) of dimethyl cyanamide in 50 ml anhydrous toluene. The mixture is then stirred for 17 hours, and then filtered under rigorously anhydrous conditions. Excess phosgene and toluene are removed under vacuum at 60° C., leaving 40.1 grams (83%) of N,N-dimethyl-N'-chlorocarbonyl carbamidoyl chloride as a pale-yellow, moisture-sensitive oil, B.P. 114°–115° C at 1.5 mm Hg. This material is of sensitive purity for use as an intermediate. This material can be further vacuum distilled but with some accompanying decomposition.

A solution of 59.0 grams (0.349 mole) of N,N-dimethyl-N'-chlorocarbonyl carbamidoyl chloride in 612 ml of tetrahydrofuran is used to treat, dropwise over a 70 minute period at −5° C., a mixture of 60.0 grams (0.349 mole) 1-cyclohexyl-3-methylthiourea and 91.0 grams (0.9 mole) triethylamine in 1346 ml tetrahydrofuran. The resulting mixture is stirred for 17 hours, filtered and the insoluble amine salt is washed with tetrahydrofuran. The solvent is stripped from the combined filtrate and tetrahydrofuran wash and the residue is washed successively with ether and water. Drying in a vacuum oven gives 82 grams, 88%, of 3-cyclohexyl-1-methyl-6-dimethylamino-2-thio-s-triazine 2,4(1H,3H)-dione, m.p. 209° C.

With the appropriate N-alkyl-N methyl cyanamide and 1-substituted-3-methylthiourea, the above procedure can be used to make the following 2-thiotriazinediones of formula I.

| Example | $R_1$ | $R_2$ | Melting Point, °C |
|---|---|---|---|
| VI a | t-butyl | methyl | 155–156 |
| b | isopropyl | methyl | 145–146 |
| c | 4-chlorophenyl | methyl | 240–241.5 |
| d | cyclohexyl | butyl | 104–105 |

Similarly, other analogs were prepared as shown below:

| Example | $R_1$ | $R_2$ |
|---|---|---|
| e | n-propyl | methyl |
| f | n-hexyl | methyl |
| g | neopentyl | methyl |
| h | 1-ethylpropyl | methyl |

| Example | $R_1$ | $R_2$ |
|---|---|---|
| i | cyclopentyl | methyl |
| j | cyclooctyl | methyl |
| k | 3-methylcyclopentyl | methyl |
| l | 3-methylcyclohexyl | methyl |
| m | 3,5-dimethylcyclohexyl | methyl |
| n | 2-cyclohexen-1-yl | methyl |
| o | decahydronapth-1-yl | methyl |
| p | phenyl | methyl |
| q | 3-trifluoromethylphenyl | methyl |
| r | 2-fluorophenyl | methyl |
| s | 3,4-dichlorophenyl | methyl |
| t | cyclohexyl | ethyl |

Formulation of the compounds

Useful formulations of the compounds of formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1976, pp. 147ff. and "Perry's Chemical Engineer's Handbook", 4th. Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1-4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE VI

| Wettable Powder | |
|---|---|
| 3-cyclohexyl-1-methyl-6-dimethylamino-2-thio-s-triazine-2,4(1H,3H)-dione | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S.N. 50 sieve (0.3 mm opening) before packaging.

All compounds of the invention may be formulated in the same manner.

EXAMPLE VII

| Extruded Pellet | |
|---|---|
| 3-isopropyl-1-methyl-6-dimethylamino-2-thio-s-triazine-2,4(1H,3H)-dione | 25% |

| -continued | |
|---|---|
| anhydrous sodium sulfate | 10% |
| crude calcium ligninsulfonate | 5% |
| sodium alkylnaphthalene-sulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held an a U.S. Ser. No. 40 sieve (0.42 mm openings) may be packed for use and the fines recycled.

EXAMPLE VIII

| Aqueous Suspension | |
|---|---|
| 3-p-chlorophenyl-1-methyl-6-dimethylamino-2-thio-s-triazine-2,4(1H,3H)-dione | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE IX

| | |
|---|---|
| 3-cyclohexyl-1-methyl-6-dimethyl amino-2-thio-s-triazine-2,4(1H,3H)-dione | 20% |
| isophorone | 67% |
| dimethylformamide | 5% |
| blend of oil soluble sulfonates and polyethyleneglycol ethers | 8% |

The above ingredients are blended with warming to produce a homogeneous emulsifiable concentrate.

EXAMPLE X

| Wettable Powder | |
|---|---|
| 3-cyclohexyl-1-methyl-6-dimethylamino-2-thio-s-triazine-2,4(1H,3H)-dione | 80% |
| dodecylphenyl polyethylene glycol ether | 2% |
| sodium ligninsulfonate | 4% |
| sodium silicoaluminate | 6% |
| kaolinite | 8% |

The ingredients are thoroughly blended. The liquid surfactant is added by spraying upon the solid ingredients in the blender. After grinding in a hammer mill to produce particles essentially all below 100 microns, the material is reblended and sifted through a U.S. Ser. No. 50 sieve (0.3 mm opening) and packaged.

EXAMPLE XI

| Granule | |
|---|---|
| wettable powder of Example X | 10% |
| attapulgite granules (U.S.S.N. 20-40; 0.84-0.42 mm) | 90% |

A slurry of wettable powder containing 50% solids is sprayed on the surface of attapulgite granules in a double-cone blender. The granules are dried and packaged.

EXAMPLE XII

| High Strength Concentrate | |
|---|---|
| 3-(3,4-dichlorophenyl)-1-methyl-6-dimethylamino-2-thio-s-triazine-2,4-(1H,3H)-dione | 99% |
| trimethylnonyl polyethylene glycol ether | 1% |

The surfactant is sprayed upon the active ingredient in a blender and the mixture sifted through a U.S. Ser. No. 40 sieve (0.42 mm openings) prior to packaging. The concentrate may be formulated further for practical use.

EXAMPLE XIII

| Dust | |
|---|---|
| high strength concentrate Example XII | 25.4% |
| pyrophyllite, powdered | 74.6% |

The ingredients are thoroughly blended and packaged for use.

Use of the Compounds

The compounds of formula I are useful for the control of undesired vegetation. They can be used wherever weed control is required, such as on industrial sites, railroad rights-of-way, and locations adjacent to crop lands.

The precise amount of the compounds of formula I to be used in any given situation will vary according to the particular end result desired, the use involved, the plant and soil involved, the formulation used, the mode of application, prevailing weather conditions, foliage density, and like factors. Since so many variables play a role, it is not possible to state a rate of application suitable for all situations. Broadly speaking, the compounds of the invention are used at levels of about 1 to about 25 kilograms per hectare. The lower rates in this range will generally be selected on lighter soils, soils low in organic matter content, or in situations where maximum persistence is not necessary.

The compounds of formula I can be combined with any other herbicide and they are particularly useful in combination with herbicides of the substituted urea, uracil, or s-triazine types for controlling a broad spectrum of weeds.

The compounds of this invention are especially useful for controlling undesired vegetation due to their low water solubility which results in longer soil residual activity. For example, 3-cyclohexyl-6-dimethylamino-1-methyl-2-thio-s-triazine-2,4(1H,3H)-dione has a water solubility of 2.6 ppm.

EXAMPLE XIV

Test Procedure

Seeds of crabgrass (Digitaria spp.), barnyardgrass (Echinochloa crusgalli), wild oats (Avena fatua), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including the cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days then all species were compared to controls and visually rated for response to treatment. A quantitative rating for type of injury was also made on a scale of 0 to 10; rating of 10 means complete kill, a rating of 0 means no injury. A qualitative rating for type of injury was also made; the letter "C" stands for chlorosis/necrosis; "B" indicates foliar burn; "D" stands for defoliation; "L" means lodging; and "G" represents growth retardation.

PLANT RESPONSE DATA

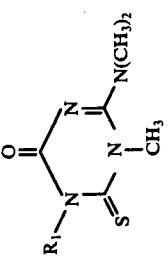

| $R_1 =$ | TYPE TESTED | kg/ha | BUSH BEAN | COT-TON | SOR-GHUM | CORN | SOY-BEAN | WHEAT | WILD OATS | RICE | BARN-YARD GRASS | CRAB-GRASS | MORNING-GLORY | COCK-LEBUR | CAS-SIA | NUTS-EDGE |
|---|---|---|---|---|---|---|---|---|---|---|---|---|---|---|---|---|
| Cyclohexyl | Pre-emergence | 2 | 10C | 10C | 10C | 10C | 10C | 10C | 10C | 10C | 10C | 10C | 10C | 10C | 10C | 9C |
| | Post-emergence | 2 | — | — | 10C | 9C | 9C | 10C | 10C | 8C | 10C | 10C | 10C | 10C | 10C | 7C |
| 4-chloro-phenyl | Pre-emergence | 0.4 | 7B | 5B | 1B | 2B | 4B | 1B | 2B | 1B | 8B | 7B | 7B | 4B | 4B | 0 |
| | Post-emergence | 0.4 | — | 7C | 10C | 9C | 5C | 10C | 10C | 3C | 10C | 10C | 9C | 4C | 10C | 5C |
| isopro-pyl | Pre-emergence | 0.4 | 7C | 8D | 8C | 6G 5L 1C 6G | 10C | 5C | 7B | 7C | 8C | 8C | 10C | 10C | 10C | 1C |
| | Post-emergence | 0.4 | — | — | 4C | | 9C | 9C | 10C | 5C | 9C | 8C | 10C | 9C | 10C | 5G |

We claim:

1. A compound of the formula:

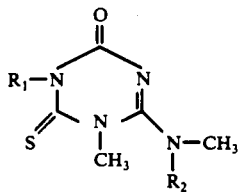

where

R₁ is alkyl of 3-6 carbons; cycloalkyl of 5-8 carbons; cycloalkyl of 5-8 carbons substituted with 1 methyl group; cyclohexyl substituted with 1 trifluoromethyl group, or with 2-4 methyl groups; cyclohexenyl; decahydronaphth-1-yl; 3-trifluoromethylphenyl; or

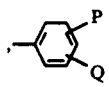

where

P is hydrogen, methyl, chlorine or fluorine; and
Q is hydrogen or chlorine; and
R₂ is alkyl of 1-4 carbons.

2. A compound of claim 1 where R₂ is methyl.

3. A compound of claim 1 where R₁ is selected from cyclopentyl, methyl-substituted cyclopentyl, cyclohexyl, trifluoromethyl-substituted cyclohexyl, methyl-substituted cyclohexyl and dimethyl-substituted cyycyclohexyl.

4. The compound of claim 1 where R₁ is cyclohexyl and R₂ is methyl.

5. A method for the control of undesired vegetation comprising applying to the locus of such undesired vegetation an herbicidally effective amount of a compound of claim 1.

6. The method of claim 5 where R₂ is methyl.

7. The method of claim 5 where R₁ is selected from cyclopentyl, methyl-substituted cyclopentyl, cyclohexyl, trifluoromethyl-substituted cyclohexyl, methyl-substituted cyclohexyl and dimethyl-substituted cyclohexyl.

8. The method of claim 5 where R₁ is cyclohexyl and R₂ is methyl.

9. A composition for the control of undesirable vegetation comprising an herbicidally effective amount of a compound of claim 1 and at least one of (a) an inert diluent and (b) a surfactant.

10. The composition of claim 9 where R₂ is methyl.

11. The composition of claim 9 where R₁ is selected from cyclopentyl, methyl-substituted cyclopentyl, cyclohexyl, trifluoromethyl-substituted cyclohexyl, methyl-substituted cyclohexyl and dimethyl-substituted cyclohexyl.

12. The composition of claim 9 where R₁ is cyclohexyl and R₂ is methyl.